United States Patent [19]

Malette

[11] Patent Number: 4,738,672
[45] Date of Patent: Apr. 19, 1988

[54] THORAX DRAINAGE APPARATUS

[76] Inventor: William G. Malette, 428 Harborview Dr. SE. #126, Bainbridge, Wash. 98110

[21] Appl. No.: 904,411

[22] Filed: Sep. 8, 1986

[51] Int. Cl.$^4$ .............................................. A61M 1/00
[52] U.S. Cl. .................................................. 604/319
[58] Field of Search .............................. 604/317–321; 137/205

[56] References Cited

U.S. PATENT DOCUMENTS

| | | | |
|---|---|---|---|
| 3,381,687 | 5/1968 | Andersen et al. | 604/321 |
| 3,463,159 | 8/1969 | Heimlich | 604/321 |
| 3,750,692 | 8/1973 | Tibbs | 137/205 |
| 3,757,783 | 9/1973 | Alley | 128/277 |
| 4,112,948 | 9/1978 | Kurtz et al. | 604/321 |
| 4,289,158 | 9/1981 | Nehring | 137/205 |
| 4,439,189 | 3/1984 | Sargeant et al. | 604/317 |
| 4,481,008 | 11/1984 | Kurtz | 604/319 |

FOREIGN PATENT DOCUMENTS 0096195 12/1983 European Pat. Off. ............ 604/321

OTHER PUBLICATIONS

"Heimlich Valve for Chest Drainage", Heimlich, H. J., M.D., Medical Instrumentation, vol. 17, No. 1, Jan.-Feb., 1983.

Primary Examiner—C. Fred Rosenbaum
Assistant Examiner—J. L. Kruter
Attorney, Agent, or Firm—Zarley, McKee, Thomte, Voorhees & Sease

[57] ABSTRACT

A collection chamber for fluids and a wide diameter pathway for the removal of air due to leaks from the lung after operation or injury to the contents of the thorax is described. The collection chamber is provided with ports for the attachment of tubing extending from the chest cavity and for connection to a vacuum pump. A water level control vacuum regulator is integral with the chamber which allows a parallel pathway for the removal of large volumes of air from the pleural space without the necessity of a high vacuum. A one-way valve is provided which is open during the drainage mode but which closes during the respiratory inhalation mode to prevent the back flow of air or fluid into the pleural space. In the event of vacuum pump failure, a pressure relief valve is provided to relieve excess positive pressure within the collection chamber.

2 Claims, 2 Drawing Sheets

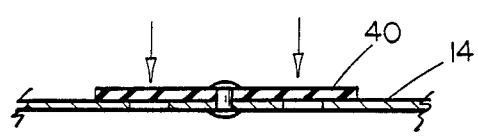
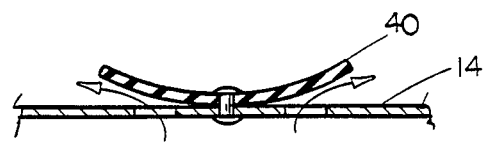
FIG. 4  FIG. 5
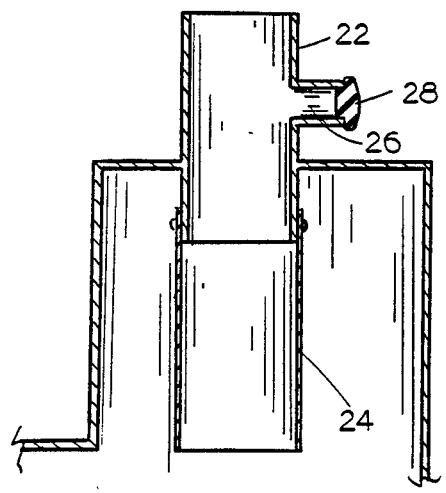
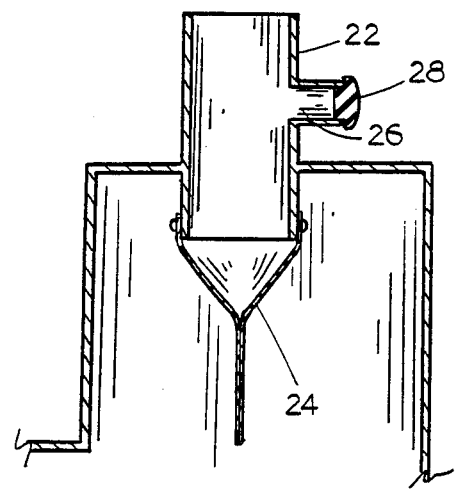
FIG. 6  FIG. 7
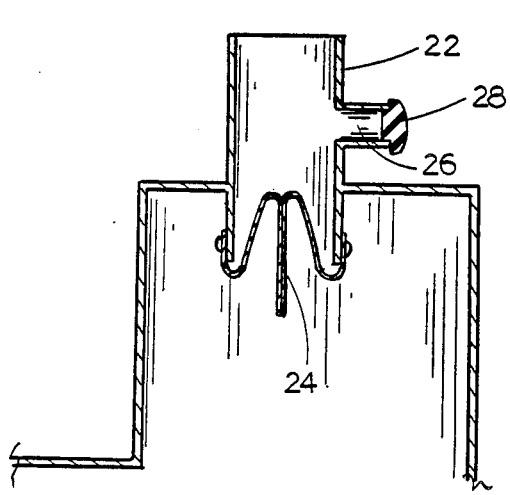
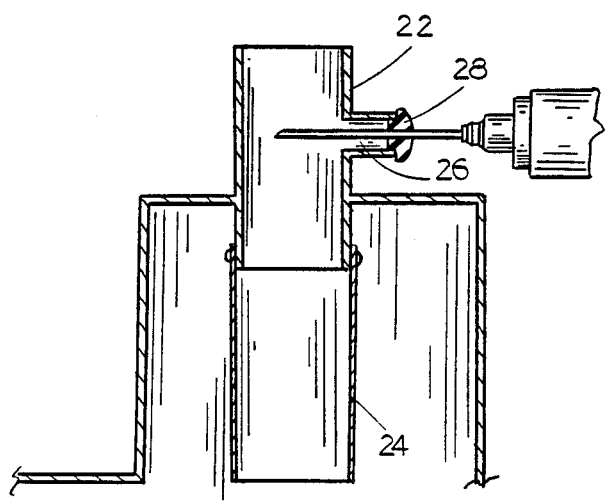
FIG. 8  FIG. 9

THORAX DRAINAGE APPARATUS

BACKGROUND OF THE INVENTION

It is necessary to drain air and fluid from the pleural space following operation or injury to organs within the thorax. If drainage of air and fluid from the pleural space is not sufficient, the lung will not be able to expand to fill the pleural space which may result in respiratory insufficiency or the development of infection. Many different types of drainage devices have been provided for draining the pleural space. One method of draining the pleural space is to insert a catheter into the chest with the distal end thereof sealed by a condom having the end removed, to a complicated system of up to five serially connected chambers having constricted connections. In the later systems, now the state of the art, a problem arises when there is a high volume air leak from the lung which is common in older patients with inherent lung disease. In such systems, high vacuum levels are required to remove such volumes of air. During normal respiration, a negative pressure is developed, with respect to atmospheric, in the pleural space. This is the result of the lowering of the diaphragm and the increased volume of the chest with the rise of the rib cage during inspiration. The normal value of the negative pressure is 3.5–8.0 centimeters of water. The volume flow of air is governed by the Hagen-Poiseuille Law which states that for a given pressure gradient and tube length, the determinant of flow rate is the radius of the tube. Anesthesiologists are acutely aware of this and breathing circuits in anesthesia are maintained as large and short as possible. When a tube ends in an abrupt manner in a chamber, the flow is no longer laminar but becomes turbulent which introduces added resistance to flow. The length of the tube (or pathway) is also important when vacuum is applied.

According to the formula:

$$C = 12.1 \frac{D^3}{L}$$

Where
D is tube diameter
L is length of tubing pathway
C is airi flow in Liters/Minute
For example:

$$L = 2.5 \text{ ft. flow} = 28.9 \text{ L/min}$$
$$L = 4.5 \text{ ft. flow} = 14.5 \text{ L/min}$$
$$L = 10.0 \text{ ft flow} = 7.2 \text{ L/min}$$

Therefore, the optimum removal of air through a chest drainage device will occur when the largest tubing diameter is combined with the shortest pathway from the pleural space to the vacuum outlet. In addition, a minimum of abrupt changes from laminar flow to turbulent flow should interrupt the pathway.

The prior art devices do not meet these criteria. The pathway is by a series of connected chambers each of which contributes turbulence. Tubing pathways are unnecessarily long and in some cases, constrictions are utilized to control flow or pressure all of which makes a high vacuum a necessity to remove a given volume of air. Since the normal negative pressure required to keep the lung inflated and allow normal respiration is low, high vacuum negates the normal respiratory efforts. High vacuum can trap the lung against the intra pleural catheter thus occluding the catheter making the catheter ineffective and resulting in collapse of the lung. In addition, high vacuum overcomes the attempt of the lung tissue to seal itself thus causing the air leaks to continue or to increase.

SUMMARY OF THE INVENTION

A thorax drainage apparatus is described which comprises a collection chamber having a first port formed in the upper end thereof which is in communication with a vacuum pump so that a negative pressure is created within the collection chamber. The collection chamber also has a second port formed therein which is adapted to be connected to a catheter tube extending to the patient's chest. A first valve is operatively mounted on the second port which is open during the respiratory exhalation mode and which is closed during the respiratory inhalation mode. A transparent column is positioned within the collection chamber and extends between the upper and lower ends thereof. The upper end of the transparent column is provided with openings formed therein to permit communication between the upper interior of the collection chamber and the upper interior of the transparent column. A hollow vent tube extends downwardly through the upper end of the collection chamber within the transparent column and has its lower end positioned above the lower end of the collection chamber. The upper end of the vent tube is in communication with the atmosphere. An exhaust port is also formed in the upper end of the collection chamber and is normally closed by a flap valve. The flap valve permits communication between the upper interior of the collection chamber and the atmosphere when a predetermined positive pressure is reached within the collection chamber. A needle port or valve is also mounted in the second port so that excess negative pressure in the catheter tubing may be relieved at times.

The level of vacuum or negative pressure within the collection chamber is regulated by the height of water in the transparent column. When that level is exceeded, outside air is drawn into the upper end of the vent tube, outwardly from the lower end of the vent tube, and thence outwardly through the openings formed in the upper end of the transparent column thereby limiting the vacuum according to the height of the water column. In the event that the vacuum pump fails in the closed position, air from the lung could build up pressure in the chamber to such a level which could collapse the lung. To prevent such lung collapse, the second valve or exhaust valve opens when the pressure within the collection chamber is greater than atmospheric pressure.

It is therefore a principal object of the invention to provide a new and improved thoracic drainage system.

More specifically, it is an object of the invention to provide a simplified system which provides the widest and shortest pathway for the removal of air and fluid from the pleural space.

It is a further object of the invention to provide an apparatus of the type described which permits the removal of excess negative pressure in the drainage tubing.

It is yet a further object of the invention to provide an apparatus of the type described including means for relieving excess pressure in the collection chamber.

Still another object of the invention is to provide a thoracic drainage apparatus including a vacuum regulation column in parallel with the main collection chamber.

These and other objects will be apparent to those skilled in the art.

BRIEF DESCRIPTION OF THE DRAWINGS

FIG. 4 is a sectional view of the exhaust valve portion of this invention;

FIG. 5 is a sectional view similar to FIG. 4 but which illustrates the exhaust valve in its open position;

FIG. 6 is a sectional view of a valve mechanism;

FIG. 7 is a sectional view similar to FIG. 6 except that the valve has closed;

FIG. 8 is a sectional view similar to FIG. 7 except that the valve has moved upwardly into its supporting port; and FIG. 9 is a sectional view illustrating the manner in which the excess negative pressure in the catheter tubing may be relieved.

DESCRIPTION OF THE PREFERRED EMBODIMENT

Figure 1:
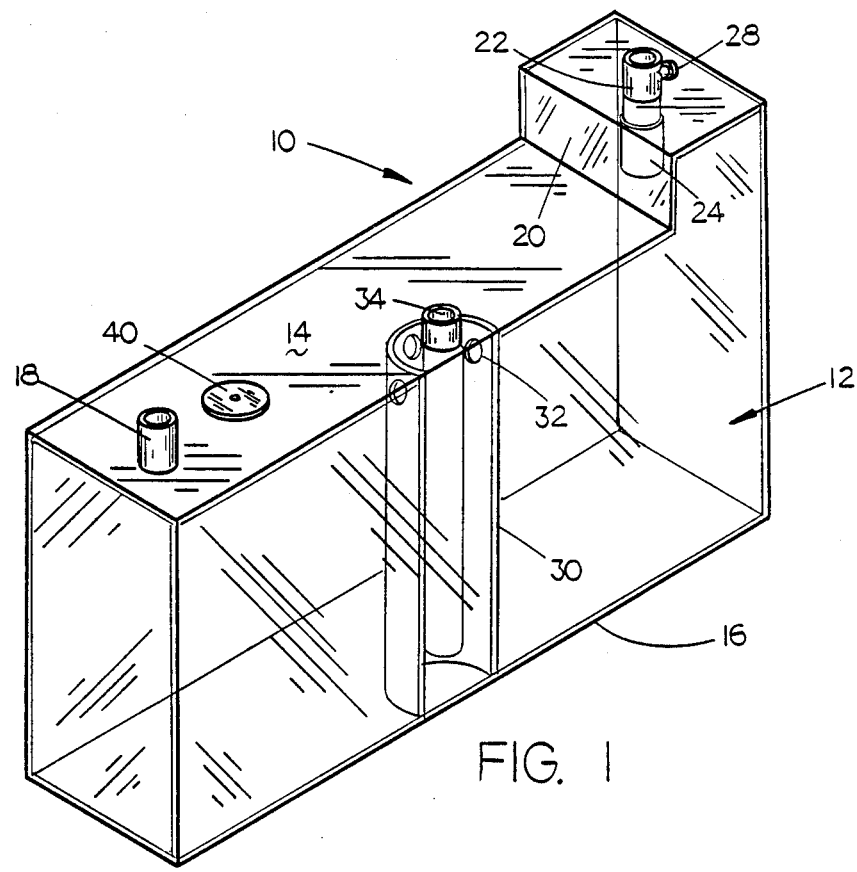
FIG. 1 is a perspective view of the apparatus of this invention.
Figure 2:
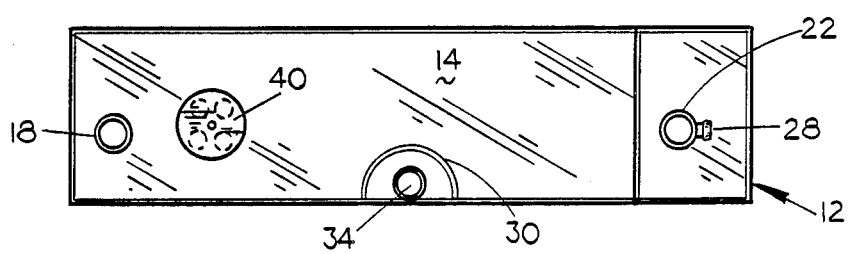
FIG. 2 is a top view of the apparatus of this invention.
Figure 3:
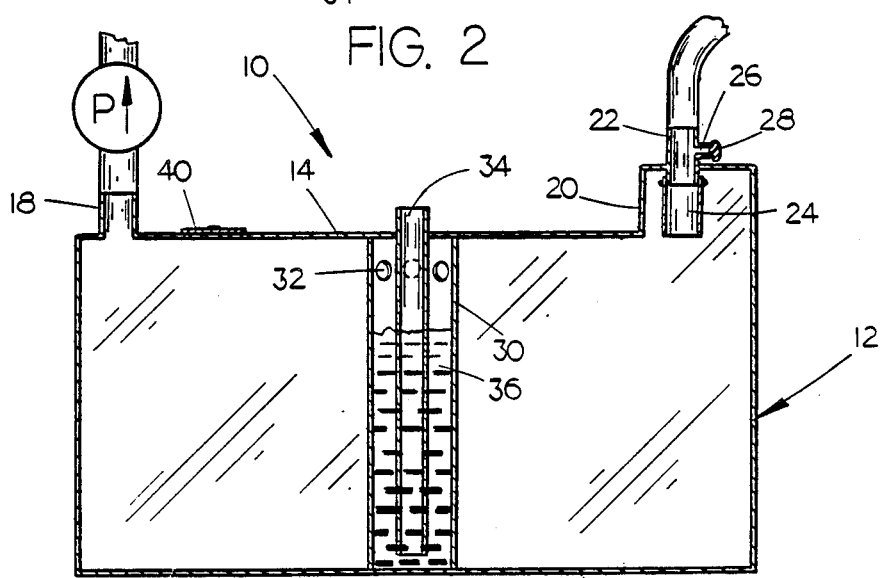
FIG. 3 is a longitudinal sectional view of the apparatus of FIGS. 1 and 2.

The thoracic drainage apparatus of this invention is referred to generally by the reference numeral 10 and includes a collection chamber or vessel 12 having an upper end 14 and lower end 16. Chamber 12 is provided with a port 18 provided at the upper end thereof which is adapted to be connected by vacuum pump for creating a negative pressure within the collection chamber.

Collection chamber 12 is provided with an upper end portion 20 positioned at one end thereof. Mounted within upper end portion 20 is a port 22 having a valve means 24 mounted on the lower end thereof within upper end portion 20. Valve means 24 is of the "condom" type which is open during the respiratory exhalation mode but which is closed during the respiratory inhalation mode. The upper end of port 22 is connected to a drainage catheter tube extending from the pleural space within the chest. The numeral 26 refers to an access port extending laterally of port 22 and having a resilient seal 28 mounted on the outer end thereof. If desired, resilient seal 28 may be replaced by a one-way check valve as will be described in greater detail hereinafter.

A transparent column 30 is positioned within collection chamber 12 and extends between the upper and lower ends thereof as seen in the drawings. The lower end of column 30 is mounted on the lower end of collection chamber 12 in a sealed relationship with respect thereto. Column 30 is provided with a plurality of openings 32 formed therein adjacent its upper end as also seen in the drawings. Vent tube 34 extends downwardly through the upper end of collection chamber 12 within column 30 as seen in the drawings. The upper end of vent tube 34 is in communication with the atmosphere. The lower end of vent tube 34 is positioned above the lower end 16 of collection chamber 12. The numeral 36 refers to water which is of a predetermined height and which is positioned between the exterior of vent tube 34 and the interior of column 30.

In use, the predetermined amount of water is positioned between tube 34 and column 30 and the port 18 is connected to the vacuum pump. The drainage catheter is connected to the port 22 and the vacuum pump is then energized. As the patient exhales, valve 24 opens to permit air and fluid to pass from the catheter tubing to the interior of the collection chamber. When the patient is in the respiratory inhalation mode, valve 24 closes to prevent the return of atmospheric air within the chamber to the pleural space. In the event that excess negative pressure is formed in the tubing extending to the chest area, a needle 38 may be extended through the resilient seal 28 to allow atmospheric air to enter the same and allow the valve 24 to re-open.

The vent tube 34 and the column 30 form a vacuum regulator. The level of vacuum or negative pressure within the collection chamber is regulated by the height of water within the column 30. When that level is exceeded, outside air or atmospheric air enters the upper interior of tube 34, downwardly within the tube 34 and outwardly from the upper end, upwardly through the water in the column 30 and thence into the interior of collection chamber through the openings 32. This arrangement is believed to be unique in that the entire column is within the main chamber obviating a serial connection by becoming a parallel pathway.

In the event of vacuum pump failure in the closed position, air from the lung could build up pressure in the collection chamber to a level which could possibly collapse the lung. To prevent lung collapse, the relief or exhaust valve 40 is provided. Exhaust valve 40 normally closes the exhaust ports 42 formed in the upper end 14 of chamber 12. When the positive pressure within the chamber reaches a predetermined level, exhaust valve 40 moves to the open position thereby preventing a pressure buildup within the storage chamber.

It can therefore be seen that a simplified system or apparatus has been provided which seals the pleural space, allows a large volume of air to be evacuated at a lower vacuum, and provides the necessary safety elements for the prevention of complications. It can therefore be seen that the invention accomplishes at least all of its stated objectives.

I claim:

1. A thorax drainage apparatus comprising,
   a collection chamber having upper and lower ends, opposite ends, and opposite sides,
   a chest catheter tube,
   said collection chamber having a first port means formed therein adjacent its upper end adjacent one end thereof which is fluidly connected to a vacuum pump for creating a negative pressure within said chamber,
   said collection chamber having a second port means formed therein adjacent its upper end adjacent its other end which is connected to said chest catheter tube,
   a first valve means in said collection chamber connected to said second port means which is movable between open and closed positions, said first valve means being in its open position during respiratory exhalation and being in its closed position during respiratory inspiration, said first valve means being positioned so as to discharge the contents of said chest catheter tube into said chamber adjacent the upper end of said chamber,
   a vertically disposed hollow vent tube extending downwardly into said chamber from the upper end thereof and having upper and lower ends, said upper end being in communication with the atmosphere, said lower end positioned above the lower end of said chamber, a vertically disposed column in said chamber having said vent tube positioned therein and peripherally sealed to said upper end, said column having a greater inside diameter than the outside diameter of said vent tube along the length thereof to enable a water column of predetermined height to be created therebetween, the lower end of said column being positioned on the lower end of said chamber in a sealed relationship with respect thereto, said column having a plurality of opening means adjacent its upper end to provide fluid communication between the interior of said column and said chamber, said chamber having an exhaust port formed therein at its upper end, and a second valve means normally closing said exhaust port but which permits atmospheric communication of the upper interior of said chamber when a predetermined positive pressure is reached within said chamber, the interior of said chamber being substantially unobstructed thereby providing direct flow between said first valve means and said first port means, whereby a substantially unobstructed air flow is permitted between said first valve means and said second port means, the interior of said chamber being unobstructed around said vent tube and said column so that ambient air entering said chamber, through said vent tube and said column, will be unrestricted except for the resistance offered by the water column between said vent tube and said column.

2. The device of claim 1 wherein said second port means comprises a vertically disposed cylindrical member having its upper end disposed above said upper end of said chamber and its lower end disposed within said chamber, and an access port in communication with the interior of said cylindrical member above said chamber and extending outwardly therefrom, and means selectively closing the outer end of said access port for permitting air to be selectively introduced into said chest catheter tube to relieve excess negative pressure in the chest catheter tube.

* * * * *